US009388434B2

(12) United States Patent
San et al.

(10) Patent No.: US 9,388,434 B2
(45) Date of Patent: Jul. 12, 2016

(54) SYNTHESIS OF SHORT CHAIN FATTY ACIDS FROM BACTERIA

(71) Applicant: William Marsh Rice University, Houston, TX (US)

(72) Inventors: Ka-Yiu San, Houston, TX (US); Songi Han, Houston, TX (US)

(73) Assignee: William Marsh Rice University, Houston, TX (US)

( * ) Notice: Subject to any disclaimer, the term of this patent is extended or adjusted under 35 U.S.C. 154(b) by 5 days.

(21) Appl. No.: 14/161,456

(22) Filed: Jan. 22, 2014

(65) Prior Publication Data

US 2014/0212935 A1 Jul. 31, 2014

Related U.S. Application Data

(60) Provisional application No. 61/757,608, filed on Jan. 28, 2013.

(51) Int. Cl.
*C12P 7/64* (2006.01)
*C12N 9/16* (2006.01)

(52) U.S. Cl.
CPC .................. *C12P 7/6409* (2013.01); *C12N 9/16* (2013.01); *C12Y 301/02014* (2013.01); *Y02P 20/52* (2015.11)

(58) Field of Classification Search
None
See application file for complete search history.

(56) References Cited

FOREIGN PATENT DOCUMENTS

WO  2011116279  12/2011
WO  2013096665  6/2013

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
U.S. Appl. No. 14/104,628, "Microbial Odd Chain Fatty Acids", filed Dec. 12, 2013.
Voelker and Davies (1994) J. Bacteriol., 176:7320-7327.
Heath and Rock (1996a) J Biol Chem, 271, 10996.
Heath and Rock (1996b) J Biol Chem, 271, 1833.
Davis and Cronan (2001) J Bacteriol, 183, 1499.
Jing F., et al., Phylogenetic and experimental characterization of an acyl-ACP thioesterase family reveals significant diversity in enzymatic specificity and activity, BMC Biochemistry 2011, 12:44.

* cited by examiner

*Primary Examiner* — Christian Fronda
(74) *Attorney, Agent, or Firm* — Boulware & Valoir

(57) ABSTRACT

The present invention relates to an engineered bacteria for producing short chain fatty acid with the overexpression of a long chain (>C12) acyl-ACP thioesterases (long-TE) and a short chain (≤C12) acyl-ACP thioesterases (short-TE).

20 Claims, 2 Drawing Sheets

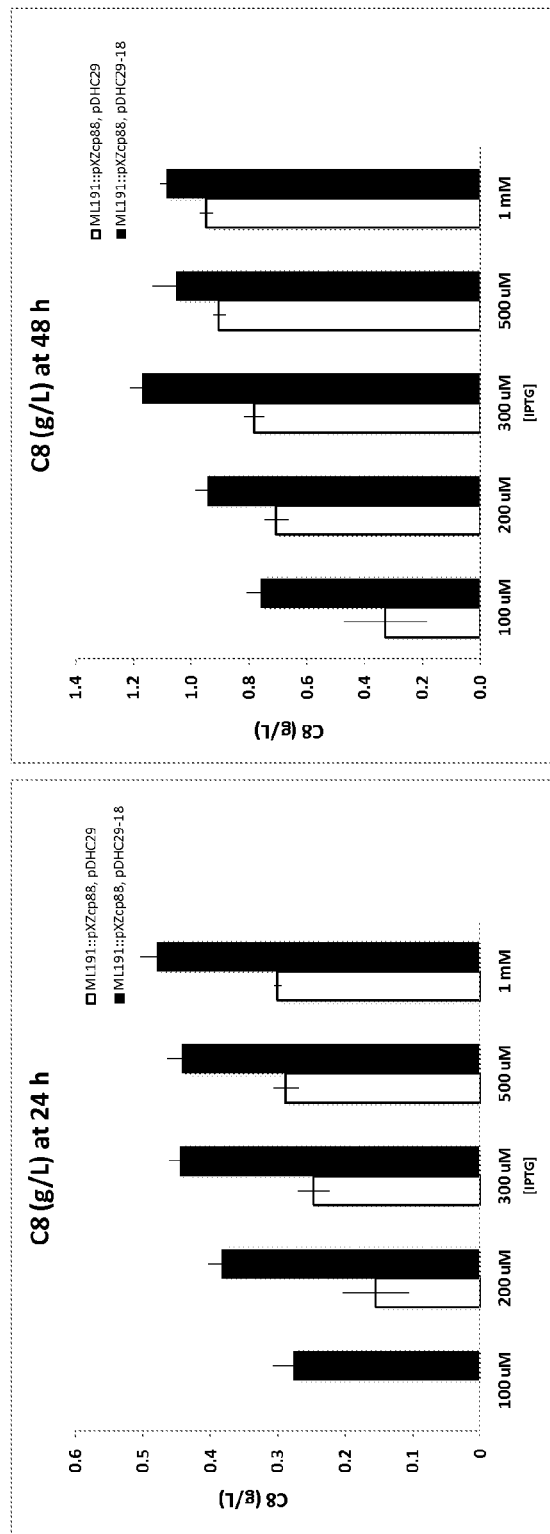
Figure 2. Comparison of the accumulation of octanoic acid by two strains; ML191::pXZcp88, pDHC29 ($\Delta fadD$ $\Delta pfkA$ short chain acyl-ACP thioesterase$^-$) and ML191::pXZcp88, pDHC29-18 ($\Delta fadD$ $\Delta pfkA$ short chain acyl-ACP thioesterase$^+$ long chain acyl-ACP thioesterase$^-$) at 24 and 48 hours.

SYNTHESIS OF SHORT CHAIN FATTY ACIDS FROM BACTERIA

PRIOR RELATED APPLICATIONS

This application claims priority to 61/757,608, filed Jan. 28, 2013, and incorporated by reference herein in its entirety for all purposes.

FEDERALLY SPONSORED RESEARCH STATEMENT

This invention was made with government support under Grant No: EEC-0813570 awarded by the NSF. The government has certain rights in the invention.

REFERENCE TO MICROFICHE APPENDIX

Not applicable.

FIELD OF THE DISCLOSURE

The disclosure relates to bacterial production and secretion of predominantly short chain fatty acids.

BACKGROUND OF THE INVENTION

Increasing energy costs and environmental concerns have emphasized the need to produce sustainable renewable fuels and chemicals. Fatty acids are composed of long alkyl chains and represent nature's "petroleum," being a primary metabolite used by cells for both chemical and energy storage functions. These energy-rich molecules are today isolated from plant and animal oils for a diverse set of products ranging from fuels to oleochemicals.

Whereas microbial fermentation processes for producing ethanol and related alcohol biofuels are well established, biodiesel (methylesters of fatty acids) is the major long chain product produced biologically, and it is almost exclusively derived from plant oils today. However, slow cycle times for engineering oil seed metabolism and the excessive accumulation of glycerol as a byproduct are two major drawbacks of deriving biodiesel from plants. Although most bacteria do produce fatty acids as cell envelope precursors, the biosynthesis of fatty acids is tightly regulated at multiple levels and large quantities are not made. Thus, the production of fatty acids from bacteria has not yet reached the point where it is cost effective.

Our laboratory has already had considerable success in engineering bacteria to produce more free fatty acids than are normally found in native bacteria. WO2011116279 for example, describes a recombinant bacterium comprising at least one overexpressed acyl-ACP thioesterase gene, and wherein at least one gene from the tricarboxylic acid cycle or glycolysis or both is inactivated to drive carbon in the direction of fat production. For example, an ACP thioesterase was combined with deletions in native fadD, and sucC. These bacteria significantly increased overall fat levels, as shown:

| Strain name | Relevant genotype | Free FA (g/l) | % improvement* | Yield (g FA/g glucose) | % improvement* |
|---|---|---|---|---|---|
| ML103_18 | ΔfadD acyl-ACP thioesterase+ | 3.12 | — | 0.21 | — |
| MLK163_18 | ΔfadD, ΔsucC acyl-ACP thioesterase+ | 3.96 | 27 | 0.27 | 29 |
| MLK211_18 | ΔfadD ΔfabR acyl-ACP thioesterase+ | 3.73 | 20 | 0.25 | 19 |
| MLK211_18A | ΔfadD ΔfabR fabA+ acyl-ACP thioesterase+ | 0.79 | −75 | 0.09 | −57 |
| MLK211_18Z | ΔfadD ΔfabR fabZ+ acyl-ACP thioesterase+ | 3.62 | 16 | 0.24 | 14 |
| MLK225_18 | ΔfadD ΔfadR acyl-ACP thioesterase+ | 2.57 | −18 | 0.17 | −19 |
| MLK225_18Z | ΔfadD ΔfadR fabZ+ acyl-ACP thioesterase+ | 3.71 | 19 | 0.25 | 19 |
| MLK227_18 | ΔfadD ΔfadR ΔfabR acyl-ACP thioesterase+ | 2.25 | −28 | 0.17 | −19 |
| ML103_18A | ΔfadD fabA+ acyl-ACP thioesterase+ | 0.44 | −86 | 0.07 | −67 |
| ML103_18Z | ΔfadD fabZ+ acyl-ACP thioesterase+ | 4.61 | 48 | 0.31 | 48 |
| ML103_18fadR | ΔfadD fadR+ acyl-ACP thioesterase+ | 4.19 | 34 | 0.27 | 29 |
| MLK212_18 | ΔfadD ΔsucC ΔfabR acyl-ACP thioesterase+ | 3.83 | 23 | 0.26 | 24 |
| MLK212_18A | ΔfadD ΔsucC ΔfabR fabA+ acyl-ACP thioesterase+ | 1.58 | −49 | 0.10 | −52 |
| MLK212_18Z | ΔfadD ΔsucC ΔfabR fabZ+ acyl-ACP thioesterase+ | 5.15 | 65 | 0.34 | 62 |
| MLK213_18 | ΔfadD ΔsucC ΔfadR acyl-ACP thioesterase+ | 2.75 | −12 | 0.19 | −10 |
| MLK213_18Z | ΔfadD ΔsucC ΔfadR fabZ+ acyl-ACP thioesterase+ | 0.32 | −90 | 0.06 | −71 |
| MLK228_18 | ΔfadD ΔsucC ΔfabR ΔfadR acyl-ACP thioesterase+ | 3.24 | 4 | 0.21 | 0 |
| MLK163_18A | ΔfadD ΔsucC fabA+ acyl-ACP thioesterase+ | 2.03 | −35 | 0.17 | −19 |

-continued

| Strain name | Relevant genotype | Free FA (g/l) | % improvement* | Yield (g FA/g glucose) | % improvement* |
|---|---|---|---|---|---|
| MLK163_18Z | ΔfadD ΔsucC fabZ+ acyl-ACP thioesterase+ | 5.65 | 81 | 0.38 | 81 |
| MLK163_18fadR | ΔfadD ΔsucC fadR+ acyl-ACP thioesterase+ | 1.49 | −52 | 0.22 | 5 | fabA+ = overexpression of FabA by plasmid, plus wild type gene present;
fabZ+ = overexpression of FabZ by plasmid, plus wild type gene present;
fadR+ = overexpression of FadR by plasmid, plus wild type gene present;
acyl-ACP thioesterase+ = overexpression of castor bean acyl ACP TE, plus wild type present.
*percentage improvement based on ML103_18

WO2013096665 describes the next step in our work, which was to engineer a microorganism for producing enhanced amounts of long chain fatty acids, having an overexpressed acyl-ACP thioesterase, and at least one mutated gene selected from the group consisting of fabR, fabZ, fadR, fabH and combinations thereof, and optionally including a inactivated sucC gene. Various bacteria in this category produce more long chain fats, some of which are shown below:

| Bacteria: | Fatty Acid Profile: |
|---|---|
| ΔfadD ΔfabR TE+ | about 60% C16:1 |
| ΔfadD ΔfadR TE+ | about 60% C14 |
| ΔfadD ΔfadR FabZ+ TE+ | about 60% C14 |
| ΔfadD FabA+ TE+ | about 90% C16 |

The next step was to enable the production of odd chain length fatty acids. Odd chain fatty acids can be made as described in U.S. application Ser. No. 14/104,628, MICROBIAL ODD CHAIN FATTY ACIDS, filed Dec. 12, 2013. In that application, the starting material was manipulated to be a C3 molecule (propionyl-CoA) by overexpressing a propionyl-CoA synthase gene. We also replaced the native β-ketoacyl-acyl carrier protein synthase III gene with one having a greater substrate preference for propionyl-coA than acetyl-coA. With these three modifications, greater odd chain fats were produced that was heretofore possible. In fact, >80% of the fats produced by such strains were of odd chain lengths. Some of the genes used therein included:

| Strain | Gene | Gene ID | Protein_ID |
|---|---|---|---|
| Salmonella enterica | prpE | 1251890 | AFD57404.1 |
| Escherichia coli | fabH | 946003 | AAC74175.1 |
| E. coli | pfkA | 948412 | AAC76898.1 |
| E. coli | fadD | 946327 | AAC74875.1 |
| Bacillus subtilis | fabH1 | 936392 | CAB12974.1 |
| Bacillus subtilis | fabH2 | 939306 | CAB12857.1 |
| Staphylococcus aureus | fabH | 1120958 | BAB57145.1 |
| Streptomyces peucetius | dpsC | L35560.1 | AAA65208.1 |
| Ricinus communis | acyl-ACP thioesterase | XM002515518 | |
| Cuphea hookeriana | acyl-ACP thioesterase | U17076 | |
| Umbellularia californica | acyl-ACP thioesterase | AAC49001 | |

The above genetic manipulations provided significant improvements in fat levels, and the excretion of visible amounts of fats also provided an easy method of collecting fats, while keeping the culture active and undisturbed, churning out more fats.

However, one improvement would be to provide a bacterium that could preferentially provide short chain fats, and another improvement would be to remove any feedback inhibition so that overall yields of short chain fats are even further increased.

SUMMARY OF THE DISCLOSURE

The present disclosure establishes an in vivo method to improve the production of short chain fatty acids, such as octanoic acid (C8), decanoic acid (C10), or dodecanoic acid (C12), by alleviating the inhibitory effect of accumulated acyl-ACP on the fatty acid synthesis pathway.

This is done by counter-intuitively adding in a long chain acyl-ACP thioesterase so that any short chain fats that escape the short chain TE are removed by the long chain TE, thus preventing feedback inhibition. The long chain fats can be secreted and collected, or used to provide cell energy via beta oxidation.

In particular, this application provides a recombinant bacterium, preferably E. coli, comprising at least one short chain and one long chain overexpressed acyl-ACP thioesterase genes, and wherein at least one gene from the tricarboxylic acid cycle or glycolysis or both is inactivated.

Therefore, the disclosure contains one or more of the following embodiments in any combination:

A bacteria having both long (>12 carbons) and short chain (≤12 carbons) acyl-ACP thioesterases added thereto.

A bacteria having overexpressed genes encoding both long and short chain acyl ACP thioesterases.

The bacteria can also comprise a reduction or deletion in at least one enzyme (or gene encoding same) in the TCA cycle and at least one enzyme of glycolysis, or both, and this will drive carbon use in the direction of fat synthesis.

The least one protein from the tricarboxylic acid cycle can be succinyl-CoA synthetase. The protein from glycolysis can be selected from glucokinase, phosphoglucose isomerase, phosphofructokinase, aldolase, triose phosphate isomerase, glyceraldehyde-3-phosphate dehydrogenase, phophoglycerate kinase, phophoglycerate mutate, enolase, pyruvate kinase, and glucose phosphotransferase.

Preferably, at least one gene from glycolysis can be glucokinase or glucose phosphotransferase.

The bacteria can further comprise at least one further modification selected from the group consisting of i) overexpressed malonyl coenzyme A-acyl carrier protein transacylase, ii) overexpressed transhydrogenase, iii) moderately overexpressed acetyl-CoA carboxylase, iv) overexpressed NAD kinase and v) reduced activity of endogenous fatty acyl-CoA synthetase.

Preferred bacteria include ΔfadD and ΔsucC, or ΔfadD and ΔpfkA.

Other additive genotypes include:

ΔfadD, ΔsucC
ΔfadD, ΔfumAC and optional ΔsucC
ΔfadD, ΔgapA and optional ΔsucC
ΔfadD, ΔptsG and optional ΔsucC
ΔfadD, ΔpfkA and optional ΔsucC
ΔfadD, Δglk and optional ΔsucC
fabD+
udhA+
pntAB+
ΔsucC
ΔfumAC and optional ΔsucC
ΔgapA and optional ΔsucC
ΔptsG and optional ΔsucC
ΔpfkA and optional ΔsucC
Δglk and optional ΔsucC
NAD-kinase+ acc+ and/or fabD+ and/or udhA+ and/or pntAB+ and/or NAD-kinase+ combined with any genotypes herein.

Methods of making short chain fatty acids are also provided comprising:
a. inoculating culture broth in a container having walls with a bacteria as herein described;
b. growing said bacteria until said bacteria secrete fatty acids into said culture broth; and
c. collecting said fatty acids.
In some embodiments, the culture broth is acidified, e.g., with 0.1-1% acetic acid.
Any suitable method of collecting the secreted fatty acids can be used, including;
a. collecting a solid fraction of said fatty acids by filtration of said culture broth;
b. extracting solids from the walls of said container with a hydrophobic solvent;
c. rinsing said walls with an alkali solution;
d. skimming said fatty acids from a top of said culture broth;
e. or combinations and variations of same.
The following abbreviations may be used herein:

| Abb | Name | Exemplary Protein Acc. Nos. |
|---|---|---|
| Pgi | phosphoglucose isomerase | AAC76995.1 |
| PfkA | phosphofructokinase A | AAC76898.1 |
| PfkB | phosphofructokinase B | AAC74793.1 |
| Aldolase | aldolase | YP_490034.1 |
| TpiA | triose phosphate isomerase | AAC76901.1 |
| GAPDH | Glyceraldehyde-3-phosphate dehydrogenase | AAA23847.1 |
| PGK | phosphoglycerate kinase | YP_491126.1 |
| PGM | phosphoglycerate mutate | AAC75963.1 |
| Enolase | enolase | YP_490987.1 |
| PK | pyruvate kinase | AAB47952.1 |
| Glucose PTS | glucose phosphotransferase system | YP_490652.1 |
| FabD+ | malonyl coenzyme A-acyl carrier protein transacylase+ | AAA23742.1 |
| UdhA+ | transhydrogenase+ | NP_418397.2 |
| PntAB+ | | YP_489865.1 BAA15342.1 |
| ACC+ | acetyl-CoA carboxylase+ | NP_414727 |
| DfadD | reduced activity of endogenous fatty acyl-CoA synthetase | YP_002999557.1 |
| ACC | Acetyl-CoA carboxylase | P24182.2 |
| ACP or acyl-ACP | Acyl-acyl carrier protein | AAB27925.2 |
| FA | Fatty acid | NA |
| FabA | beta-hydroxydecanoyl thioester dehydrase | ABJ00363.1 |
| FabB | Component of β-ketoacyl-ACP synthase I | EHY18746.1 |
| FabD | malonyl CoA-acyl carrier protein transacylase | YP_489360.1 |
| FabH | component of β-ketoacyl-acyl carrier protein synthase III | EGT67886.1 |
| FabZ | R)-hydroxymyristol acyl carrier protein dehydratase | AAY89693.1 |
| FadD | fatty acyl-CoA synthetase | EHY19478.1 |
| FadR | Repressor/activator for fatty acid metabolism regulon | CAA30881.1 |
| FumAC | fumarase A, fumarase C | YP_006173189.1 and YP_489874.1 |
| GapA | component of glyceraldehyde 3-phosphate dehydrogenase-A complex | YP_490040.1 |
| Glk | glucokinase | EDV65543.1 |
| GltA | citrate synthase | YP_006128080.1 |
| IPTG | Isopropyl β-d-1-thiogalactopyranoside | NA |
| LB | Luria-Bertoni | NA |
| NADK | NAD Kinase, aka yfjB | AAC75664.1 |
| PfkA | 6-phosphofructokinase-1 | CAA26356.1 |
| PtsG | glucose phosphotransferase enzyme IIBC aka glucose permease | EHY19964.1 |
| pykF | Gene encoding a component of pyruvate kinase I | YP_489938.1 |
| sucC | succinyl-CoA synthetase subunit beta | EFF01582.1 |
| Short TE | Acyl-ACP Thioesterase with preference for short chain FAs | AAC49269.1 (*Cuphea hookeriana*) AAC49179.1 (*Cuphea palustris*) |
| Long TE | Acyl-ACP Thioesterase with preference for long chain FAs | ABV54795.1 (*Ricinus communis*) ABU96744.1 (*Jatropha curcas*) AAX51636.1 (*Diploknema butyracea*) AAF02215.1 or AF076535.1 (*Gossypium hirsutum*) |
| TERc | Thioesterase from *Ricinus communis* | XP_002515564.1 XM002515518 |
| udhA aka SthA | pyridine nucleotide transhydrogenase, soluble, more commonly called SthA | CAA46822.1 |
| TEhyb | Hybrid TE from *Ricinus* and *Cuphea* | As described in WO2011116279 |

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

As used herein, the expressions "microorganism," "bacteria", "strain" and the like may be used interchangeably and all such designations include progeny. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

Reference to proteins herein can be understood to include reference to the gene encoding such protein. Thus, a claimed "permease" protein can include the related gene encoding that permease. However, it is preferred herein to refer to the protein by standard name per ecoliwiki, e.g. Pgi is glucose-phosphate isomerase, since both enzymatic and gene names have varied widely in the prokaryotic arts.

"Operably associated" or "operably linked", as used herein, refer to functionally coupled nucleic acid or amino acid sequences.

"Recombinant" is relating to, derived from, or containing genetically engineered material. In other words, the genome was intentionally manipulated in some way.

"Reduced activity" or "inactivation" is defined herein to be at least a 75% reduction in protein activity, as compared with an appropriate control species. Preferably, at least 80, 85, 90, 95% reduction in activity is attained, and in the most preferred embodiment, the activity is eliminated (100%). Proteins can be inactivated with inhibitors, by mutation, or by suppression of expression or translation, by knock-out, by adding stop codons, by frame shift mutation, and the like.

By "null" or "knockout" what is meant is that the mutation produces undetectable active protein. A gene can be completely (100%) reduced by knockout or removal of part of all of the gene sequence. Use of a frame shift mutation, early stop codon, point mutations of critical residues, or deletions or insertions, and the like, can also completely inactivate (100%) gene product by completely preventing transcription and/or translation of active protein. All null mutants herein are signified by Δ.

"Overexpression" or "overexpressed" is defined herein to be at least 150% of protein activity as compared with an appropriate control species. Preferably, the activity is increased 100-500%. Overexpression can be achieved by mutating the protein to produce a more active form or a form that is resistant to inhibition, by removing inhibitors, or adding activators, and the like. Overexpression can also be achieved by removing repressors, adding multiple copies of the gene to the cell, or up-regulating the endogenous gene, and the like. All overexpressed genes or proteins are signified herein by "+".

Acyl-acyl carrier protein (ACP) thioesterase is an enzyme that terminates the intraplastidial fatty acid synthesis in plants by hydrolyzing the acyl-ACP intermediates and releasing free fatty acids to be incorporated into glycerolipids. These enzymes are classified in two families, FatA and FatB, which differ in amino acid sequence and substrate specificity. Generally speaking, the N terminal (aa 1-98) of any acyl-ACP thioesterases controls the substrate specificity of the enzyme, and it is known how to change substrate specificity by swapping amino terminal domains.

Many acyl-ACP thioesterase proteins are known and can be added to bacteria for use in the invention (e.g., CAA52070, YP_003274948, ACY23055, AAB71729, BAB33929, to provide the accession numbers for a few of the thousands of such proteins available), although we have used plasmids encoded plant genes herein. Such genes can be added by plasmid or other vector, or can be cloned directly into the genome.

Other acyl-ACP thioesterases include *Umbellularia californica* (AAC49001), *Cinnamomum camphora* (Q39473), *Umbellularia californica* fatty acyl-ACP thioesterase (Q41635), *Myristica fragrans* (AAB71729), *Myristica fragrans* (AAB71730), *Elaeis guineensis* (ABD83939), *Elaeis guineensis* (AAD42220), *Populus tomentosa* (ABC47311), *Arabidopsis thaliana* (NP 172327), *Arabidopsis thaliana* (CAA85387), *Arabidopsis thaliana* (CAA85388), *Gossypium hirsutum* (Q9SQI3), *Cuphea lanceolata* (CAA54060), *Cuphea hookeriana* (AAC72882), *Cuphea calophylla* subsp. *mesostemon* (ABB71581), *Cuphea lanceolata* (CAC19933), *Elaeis guineensis* (AAL15645), *Cuphea hookeriana* (Q39513), *Gossypium hirsutum* (AAD01982), *Vitis vinifera* (CAN81819), *Garcinia mangostana* (AAB51525), *Brassica juncea* (ABI18986), *Madhuca longifolia* (AAX51637), *Brassica napus* (ABH11710), *Oryza sativa* (indica cultivar-group) (EAY86877), *Oryza sativa* (japonica cultivar-group) (NP-001068400), *Oryza sativa* (indica cultivar-group) (EAY99617), and *Cuphea hookeriana* (AAC49269).

In some embodiments, at least one acyl-ACP thioesterase gene is from a plant, for example overexpressed TE from *Ricinus communis* (XP_002515564.1), *Jatropha curcas* (ABU96744.1), *Diploknema butyracea* (AAX51636.1), *Cuphea palustris* (AAC49180.1), or *Gossypium hirsutum* (AAF02215.1 or AF076535.1), or an overexpressed hybrid TE comprising different thioesterase domains operably fused together (see WO2011116279, all sequences expressly incorporated by reference herein). Preferably, the hybrid thioesterase includes an amino terminal region (~aa 1-98 controls substrate specificity) of the acyl-ACP thioesterase from *Ricinus communis* or a 70, 80, 90 or 95% homolog thereto, or any TE with the desired substrate specificity, operably coupled to the remaining portion of the thioesterase from another species. In such manner, enzyme specificity can be tailored for the use in question.

A great number of TE proteins were characterized by Jing, and some of his results reproduced here:

| Kingdom | Subfamily | ACC No./Name | Organism | Rationale for synthesis[a] | Total FA[b] (nmol/mL) |
|---|---|---|---|---|---|
| Planta | A | AAC49179[c,d] | *Cuphea palustris* | A (Bimodal specificity for C8 and C10 substrates) [1] | 708 ± 45 |
| | | AAB71731 | *Ulmus americana* | A (Broad specificity; highest activity on C10 and C16) [13] | 1098 ± 62 |
| | | AAG43857 | *Iris germanica* | B | 261 ± 20 |
| | | AAG43858 | *Iris germanica* | B | 14.8 ± 4.6 |
| | | EER87824 | *Sorghum bicolor* | B (Member of a Subfamily A Poeceae TE cluster) | 126 ± 13 |
| | | EER88593 | *Sorghum bicolor* | B (Member of a Subfamily A Poeceae TE cluster) | 90.7 ± 8.0 |
| | | CnFatB1 | *Cocos nucifera* | C | 130 ± 12 |
| | | CnFatB2 | *Cocos nucifera* | C | 572 ± 32 |
| | | CnFatB3 | *Cocos nucifera* | C | 200 ± 11 |
| | | CvFatB1 | *Cuphea viscosissima* | C | 79.2 ± 9.7 |
| | | CvFatB2 | *Cuphea viscosissima* | C | 249 ± 9 |
| | | CvFatB3 | *Cuphea viscosissima* | C | 18.9 ± 2.1 |
| | | AAD42220 | *Elaeis guineensis* | C | 36.7 ± 3.8 |
| | B | EDQ65090 | *Physcomitrella patens* | B (Member of novel plant subfamily) | 380 ± 29 |
| | | EER96252 | *Sorghum bicolor* | B (Member of novel plant subfamily) | 175 ± 11 |

-continued

| Kingdom | Subfamily | ACC No./ Name | Organism | Rationale for synthesis[a] | Total FA[b] (nmol/mL) |
|---|---|---|---|---|---|
| | | EES11622 | *Sorghum bicolor* | B (Member of novel plant subfamily) | 9.43 ± 2.03 |
| | D | EEH52851 | *Micromonas pusilla* | B | 16.3 ± 1.6 |
| Bacteria | E | ACL08376 | *Desulfovibrio vulgaris* | D (Medium-chain linear, branched, and hydroxy fatty acids) [29] | 330 ± 9 |
| | F | CAH09236 | *Bacteroides fragilis* | D (Hydroxy fatty acids) [29] | 215 ± 6 |
| | | ABR43801 | *Parabacteroides distasonis* | D (Branched and branched hydroxy fatty acids) [30] | 70.3 ± 4.4 |
| | | AAO77182[e] | *Bacteroides thetaiotaomicron* | D (Anteiso-branched and hydroxy fatty acids) [29] | 60.4 ± 2.9 |
| | G | ABG82470 | *Clostridium perfringens* | D (Medium-chain fatty acids) [31] | 72.0 ± 9.5 |
| | H | EEG55387 | *Clostridium asparagiforme* | B | 25.9 ± 4.2 |
| | | EET61113 | *Bryantella formatexigens* | B | 381 ± 3 |
| | I | EDV77528 | *Geobacillus sp.* | D (Iso-branched fatty acids) [32] | 64.9 ± 12.0 |
| | J | BAH81730 | *Streptococcus dysgalactiae* | D (Medium-chain and cyclic propane ring fatty acids) [29] | 623 ± 14 |
| | | ABJ63754 | *Lactobacillus brevis* | D (Medium-chain and cyclic propane ring fatty acids) [33] | 710 ± 10 |
| | | CAD63310[e] | *Lactobacillus plantarum* | D (Medium-chain 3'-hydroxy fatty acids) [33, 34] | 436 ± 10 |
| | Non-grouped | EEI82564 | *Anaerococcus tetradius* | D (Organism produces butyric acid) [35] | 1381 ± 146 |
| | | CAE80300 | *Bdellovibrio bacteriovorus* | D (Straight-chain odd-numbered fatty acids) [29] | 333 ± 18 |
| | | ABN54268 | *Clostridium thermocellum* | D (Branched-chain fatty acids) [29] | 97.7 ± 3.2 |

[a]A: Functionally characterized TEs; B: TE does not group near characterized TEs and/or no organism lipid profile information is available; C: TEs cloned from organisms known to produce MCFAs; D: Organism's lipid profile used and predominant fatty acid constituents identified in the organism are listed in parentheses.
[b]The data are represented as mean ± standard error (n = 4).
[c]All but the three *C. nucifera* sequences were codon-optimized for expression in *E. coli*.
[d] Transit peptides were removed from all plant sequences.
[e]Acyl-ACP TEs with known crystal structures.
TEs were expressed in *E. coli* K27, and free fatty acids (FAs) that accumulated in the medium were analyzed by GC-MS.

Thus it can be seen that hundreds of such TE proteins have been used, and are readily available for overexpression uses in the claimed bacteria.

In certain species it is also possible to genetically engineer the endogenous protein to be overexpressed by changing the regulatory sequences or removing repressors. However, overexpressing the gene by inclusion on selectable plasmids that exist in hundreds of copies in the cell may be preferred due to its simplicity, although permanent modifications to the genome may be preferred in the long term for genetic stability reasons.

By "long chain" acyl-ACP thioesterase, what is meant herein, is that the TE produces a preponderance of long chain (>C12) fatty acids. Preferably, such TE produces more than 50% of a fatty acid >C12.

By "short chain" acyl-ACP thioesterase, what is meant herein, is that the TE produces a preponderance of short chain (≤C12) fatty acids. Preferably, such TE produces more than 50% of a fatty acid ≤C12.

BRIEF DESCRIPTION OF THE DRAWINGS

FIG. 2 is the comparison of the accumulation of octanoic acid by two strains; ML191::pXZcp88, pDHC29 (ΔfadD ΔpfkA short chain acyl-ACP thioesterase+) and ML191::pXZcp88, pDHC29-18 (ΔfadD ΔpfkA short chain acyl-ACP thioesterase+ long chain acyl-ACP thioesterase+) at 24 and 48 hours.

DETAILED DESCRIPTION

Figure 1:
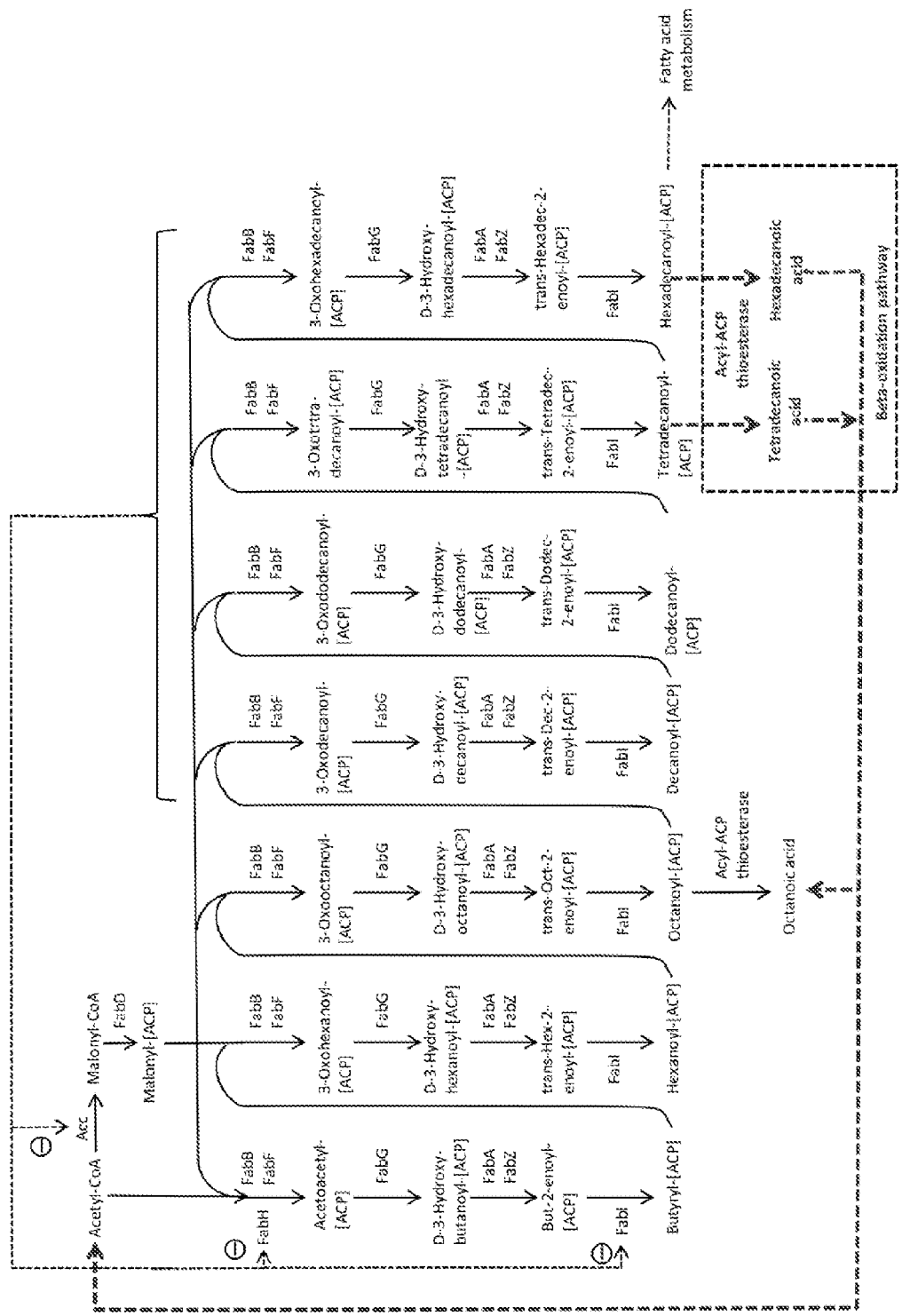
FIG. 1 illustrates a schematic of fatty acid synthesis pathway from acetyl-CoA as an example of producing octanoic acid by introducing an acyl-ACP thioesterase specific to octanoyl-ACP.

Wild type *E. coli* strains produce fatty acids mainly for the biosynthesis of lipids and cell membranes. Unlike most oleaginous microorganisms or plants, which naturally accumulate significant quantity of free fatty acids, *E. coli* normally does not accumulate free fatty acids as intermediates in lipid biosynthesis (Voelker and Davies, 1994). This is true of many, if not all, bacteria.

Free fatty acids can be produced, however, by introducing an acyl-ACP thioesterase gene in *E. coli*. The presence of the acyl-ACP thioesterase will break the fatty acid elongation cycle and release free fatty acids. Our prior work showed considerable success with this method, especially when combined with reduced gene/protein activity from at least one tricarboxylic acid cycle enzyme, or ii) at least one glycolysis enzyme, thus driving carbon in the direction of fat production. See e.g., WO2011116279.

In designing efficient free fatty acid production strains, it is necessary to increase the carbon flux to the fatty acid synthesis cycle exceeding that of the normal level needed for membrane/lipid formation. This increase will not cause a major problem for longer chain length fatty acids, as we have shown previously that we can achieve high yield high rate production.

However, for shorter chain length fatty acids and if the acyl-ACP thioesterase cannot remove all of the acyl-ACP as free fatty acid at the shorter chain length, longer chain length acyl-ACP will continue to accumulate and will subsequently increase the feedback inhibitory pressure, leading to a decrease in fatty acid synthesis or eventually completely shutting down its synthesis.

Previous studies have shown that the activity of several key enzymes with respect to fatty acid biosynthesis would be blocked by acyl-ACP through feedback inhibition (Davis and Cronan, 2001). A number of in vitro studies also have shown that the first enzyme of the fatty acid biosynthetic pathway, acetyl-CoA carboxylase encoded by accABCD, is one of the targets inhibited by acyl-ACP. In addition to acetyl-CoA carboxylase, it has suggested enoyl-ACP reductase and 3-ketoacyl-ACP synthase III encoded by fabI and fabH respectively are inhibited by feedback inhibition (Heath and Rock, 1996a, Heath and Rock, 1996b).

FIG. 1 illustrates a schematic of fatty acid synthesis pathway from acetyl-CoA as an example of producing octanoic acid by introducing an acyl-ACP thioesterase specific to octanoyl-ACP. In this case, C10-ACP, C12-ACP, C14-ACP and C16-ACP will continue to form and accumulate if their formation rates exceed that of fatty acid metabolism. The accumulated fats will elongate and/or feedback inhibit the entire pathway. Concept of alleviating the effect of acyl-ACP feedback inhibition is shown in the box using the production of octanoic acid as an example.

One obvious solution to the feedback inhibition problem is to use feedback insensitive enzymes. However, feedback insensitive enzymes are frequently not readily available. Moreover, a majority of engineered enzymes exhibit decreased reaction rates. Thus, our efforts in this direction have not proven fruitful, and although an obvious method of addressing the feedback inhibition problem, the method has proven quite unsatisfactory to solve the problem.

This invention thus represents a completely new approach to alleviate the feedback inhibition effect by counter-intuitively introducing a longer chain length acyl-ACP thioesterase (FIG. 1 dotted box) thus allowing the production of more short chain fats!

We postulate that the longer chain length acyl-ACP thioesterase serves at least two functions: 1) it provides a strong pull and thus increases the carbon flux to the fatty acid synthesis cycle; 2) the longer chain length free fatty acids serve as a sink for the longer-chain length acyl-ACPs, thus reducing their inhibitory effect. A scheme to recycle the longer chain length free fatty acids using the beta-oxidation pathway is also included in FIG. 1. Steps involved include: 1) introduction of a longer chain specific acyl-ACP thioesterase to produce longer chain free fatty acids; 2) optionally the longer chain fatty acids can be recycled back to either acetyl-CoA or to shorter chain fatty acids through the beta-oxidation pathway.

To demonstrate the concept, we used a previously constructed host strain *E. coli* strain, ML191 (MG1655, ΔfadD ΔpfkA), for short-chain fatty acid production. This strain is exemplary only, and many other strains could be used to demonstrate the value of the invention. Further, the invention can be easily applied to other species of bacteria, such as *Streptomyces, Staphlococcus, Bacillus, Haemophilus, Psuedomonas, Agrobacterium*, and the like, since cloning vectors, codon optimization, and even complete genome sequences are available for several hundreds of species. Further, fatty acid synthesis, TCA and glycolytic pathways are found in all bacteria.

Three plasmid systems were used in this work:

One plasmid, pXZcp88, carries an acyl-ACP thioesterase (a hybrid TE with target/leader from *Ricinus* and remainder from *Cuphea* described in WO2011116279, SEQ ID NO. 3) specific to shorter chain length (C8) acyl-ACP. The expression of this thioesterase is under the control of an IPTG inducible trc promoter system.

The second plasmid, pDHC29, is an expression vector, which will serve as a control.

The third plasmid, pDHC29-18 carries an acyl-ACP thioesterase (Acc. No. XM002515518 from *Ricinus communis*, a palmitoyl-acyl carrier protein thioesterase) specific to longer chain (C16) length acyl-ACP using pDHC29 as the cloning vector. The expression of this thioesterase is under the control of an IPTG inducible lac promoter system. The results of this system are shown in FIG. 2 and Table 1a and 1b.

TABLE 1a

Percentage improvement of octanoic acid production at various inducer concentrations due to the presence of the longer chain length acyl-ACP thioesterase

| | Octanoic acid (g/L) IPTG @ | | | | |
|---|---|---|---|---|---|
| Strain name | 100 μM | 200 μM | 300 μM | 500 μM | 1000 μM |
| 24 hr | | | | | |
| ML191::pXZcp88, pDHC29 | ND | 0.155 | 0.247 | 0.288 | 0.300 |
| ML191::pXZcp88, pDHC29-18 | 0.276 | 0.383 | 0.445 | 0.443 | 0.479 |
| % improvement | — | 147 | 80 | 54 | 59 |
| 48 hr | | | | | |
| ML191::pXZcp88, pDHC29 | 0.329 | 0.706 | 0.783 | 0.904 | 0.950 |
| ML191::pXZcp88, pDHC29-18 | 0.761 | 0.945 | 1.168 | 1.051 | 1.087 |
| % improvement | 131 | 34 | 49 | 16 | 14 |

ML191::pXZcp88, pDHC29 = ΔfadD ΔpfkA short chain acyl-ACP thioesterase+
ML191::pXZcp88, pDHC29-18 = ΔfadD ΔpfkA short chain acyl-ACP thioesterase+ long chain acyl-ACP thioesterase+

TABLE 1b

Percentage improvement of octanoic acid yield (g of octanoic acid produced per g of glucose consumed) at various inducer concentrations due to the presence of the longer chain length acyl-ACP thioesterase

| | Yield (g of octanoic acid produced per g of glucose consumed) IPTG @ | | | | |
|---|---|---|---|---|---|
| Strain name | 100 μM | 200 μM | 300 μM | 500 μM | 1000 μM |
| 24 hr | | | | | |
| ML191::pXZcp88, pDHC29 | | 0.046 | 0.077 | 0.106 | 0.095 |
| ML191::pXZcp88, pDHC29-18 | | 0.143 | 0.128 | 0.159 | 0.142 |
| % improvement (yield) | — | 212 | 67 | 50 | 49 |
| 48 hr | | | | | |
| ML191::pXZcp88, pDHC29 | 0.031 | 0.069 | 0.083 | 0.094 | 0.096 |
| ML191::pXZcp88, pDHC29-18 | 0.109 | 0.121 | 0.147 | 0.138 | 0.145 |
| % improvement (yield) | 250 | 73 | 78 | 46 | 52 |

ML191::pXZcp88, pDHC29 = ΔfadD ΔpfkA short chain acyl-ACP thioesterase+
ML191::pXZcp88, pDHC29-18 = ΔfadD ΔpfkA short chain acyl-ACP thioesterase+ long chain acyl-ACP thioesterase+

The strain carrying the longer chain length specific acyl-ACP thioesterase, ML191::pXZcp88, pDHC29-18 (ΔfadD ΔpfkA short chain acyl-ACP thioesterase+ long chain acyl-ACP thioesterase+), consistently outperforms the strain without, ML191::pXZcp88, pDHC29 (ΔfadD ΔpfkA short chain acyl-ACP thioesterase+) at both time points (24 and 48 h) and at all IPTG concentrations in terms of octanoic production. At an IPTG concentration of 300 μM, the production of octanoic acid (C8) is the highest among all conditions when the cells carry a longer chain fatty acyl-ACP thioesterase, showing 49% improvement over the cells without the long chain fatty acyl-ACP thioesterase (FIG. 2 and Table 1a).

In addition, the strain carrying the longer chain length specific acyl-ACP thioesterase, ML191::pXZcp88, pDHC29-18 (ΔfadD ΔpfkA short chain acyl-ACP thioesterase+ long chain acyl-ACP thioesterase+), consistently gives a higher octanoic yield (g of octanoic acid produced per g of glucose consumed) than strain ML191::pXZcp88, pDHC29 (ΔfadD ΔpfkA short chain acyl-ACP thioesterase+) at both time points (24 and 48 h) and at all IPTG concentrations (Table 1b).

In summary, we have surprisingly observed increased short chain length fatty acid, octanoic acid, production and yield by introducing a longer chain length specific acyl-ACP thioesterase.

METHODS & RESULTS

LB medium supplemented with 15 g/L glucose as a carbon source and 100 mg/L ampicillin and 35 mg/L chloramphenicol for selection were used for culturing cells. Isopropyl-β-D-thiogalactopyranoside (IPTG) was added to the medium to a final concentration of 0, 100, 200, 300, 500 μM and 1 mM for inducing the expression of appropriate acyl-ACP thioesterases. 1% of inoculum was transferred into the flask containing 50 ml LB and cultured at 30° C., 250 rpm for 48 hours. Samples were taken at three specific time points (0, 24, and 48 hr) for quantifying the fatty acids produced.

The results are shown in FIG. 2, as well as in Tables 1a and 1b. Greatly increased levels of fats were produced in strains having both long and short chain TE, and increases of up to 50% more short chain (C8) fats were produced.

Therefore, when high levels of short chain fatty acids are desired, it is helpful to add a long chain TE in order to remove any fats that escape the short chain TE, and thus prevent feedback inhibition of FA synthesis. This counter-intuitive method can result in 125% short chain fat levels, and even as high as 150%, as compared with control bacteria lacking the second long chain TE.

The method can be applied to any of the bacteria already exemplified by our lab for fatty acid synthesis, including all those described in WO2011116279 and WO2013096665 and in Ser. No. 14/104,628, MICROBIAL ODD CHAIN FATTY ACIDS, filed Dec. 12, 2013, as well as to other bacteria in the prior art or to be invented in the future. Exemplary bacteria are shown as follows:

| Species | Genotype | Acc. no and/or vector |
|---|---|---|
| B. subtilis | ΔfadD ΔpfkA short TE+, long TE+ | CAA99571.1, YP_007534906.1, pXZcp88, pDHC29 |
| S. enterica | ΔpfkA short TE+, long TE+ | EDZ28622.1, pXZcp88, pDHC29 |
| S. aureus | ΔfadD ΔpfkA short TE+, long TE+ | YP_492941.1, NP_374809.1, pXZcp88, pDHC29 |

The following references are incorporated herein in their entirety for all purposes.
WO2011116279
WO2013096665
61/740,959, filed Dec. 21, 2012 and Ser. No. 14/104,628, MICROBIAL ODD CHAIN FATTY ACIDS, filed Dec. 12, 2013.
Davis, M. S.; Cronan, J. E., Jr. J Bacteriol 2001, 183, 1499.
Heath, R. J.; Rock, C. O. J Biol Chem 1996a, 271, 10996.
Heath, R. J.; Rock, C. O. J Biol Chem 1996b, 271, 1833.
Voelker T A, Davies H M. J. Bacteriol. 1994. 176:7320-7327.
Jing F., et al., Phylogenetic and experimental characterization of an acyl-ACP thioesterase family reveals significant diversity in enzymatic specificity and activity, BMC Biochemistry 2011, 12:44.

We claim:

1. A genetically engineered E. coli comprising an overexpressed gene encoding i) a long chain (>C12) acyl-ACP thioesterases (long-TE) and ii) an overexpressed gene encoding a short chain (≤C12) acyl-ACP thioesterases (short TE), wherein said bacteria makes more short chain free fatty acids than a control strain lacking i).

2. The bacteria of claim 1, further comprising a reduction in activity of at least one enzyme in the TCA cycle and at least one enzyme of glycolysis.

3. The bacteria of claim 2, wherein said at least one protein from the tricarboxylic acid cycle is succinyl-CoA synthetase.

4. The bacteria of claim 2, wherein said at least one protein from glycolysis is selected from glucokinase, phosphoglucose isomerase, phosphofructokinase, aldolase, triose phosphate isomerase, glyceraldehyde-3-phosphate dehydrogenase, phosphoglycerate kinase, phophoglycerate mutate, enolase, pyruvate kinase, and glucose phosphotransferase.

5. The bacteria of claim 2, wherein said at least one enzyme from glycolysis is glucokinase or glucose phosphotransferase.

6. The bacteria of claim 2, further comprising at least one further modification selected from the group consisting of i) overexpressed malonyl coenzyme A-acyl carrier protein transacylase, ii) overexpressed transhydrogenase, iii) moderately overexpressed acetyl-CoA carboxylase, iv) overexpressed NAD kinase and v) reduced activity of endogenous fatty acyl-CoA synthetase.

7. The bacteria of claim 1, further comprising ΔfadD and ΔsucC.

8. The bacteria of claim 1, further comprising ΔfadD and ΔpfkA.

9. The bacteria of claim 1, having a genotype further comprising:

| |
|---|
| ΔfadD, ΔsucC |
| ΔfadD, ΔfumAC and optional ΔsucC |
| ΔfadD, ΔgapA and optional ΔsucC |
| ΔfadD, ΔptsG and optional ΔsucC |
| ΔfadD, ΔpfkA and optional ΔsucC |
| ΔfadD, Δglk and optional ΔsucC |
| TE+ and fabD+ |
| TE+ and udhA+ |
| TE+ and pntAB+ |
| ΔsucC |
| ΔfumAC and optional ΔsucC |
| ΔgapA and optional ΔsucC |
| ΔptsG and optional ΔsucC |
| ΔpfkA and optional ΔsucC |
| Δglk and optional ΔsucC |
| NAD-kinase+ | acc+ and/or fabD+ and/or udhA+ and/or pntAB+ and/or NAD-kinase+ combined with any genotypes in this table.

10. A genetically engineered bacteria comprising i) an overexpressed long chain (>C12) acyl-ACP thioesterases (long-TE) and an ii) overexpressed short chain (≤C12) acyl-ACP thioesterases (short-TE), wherein said bacteria makes more short chain free fatty acids than a control strain lacking i).

11. The bacteria of claim 10, wherein said bacteria makes 50% more short chain free fatty acids than said control strain.

12. A genetically engineered bacteria comprising I an overexpressed long chain (>C12) acyl-ACP thioesterases (long-TE) and ii) an overexpressed short chain (≤C12) acyl-ACP thioesterases (short-TE), and iii) wherein at least one gene from the tricarboxylic acid cycle or glycolysis, or both, is inactivated, wherein said bacteria makes more short chain fatty acids than a control strain lacking i).

13. A method of making short chain fatty acids, comprising:
  a) inoculating culture broth in a container having walls with a bacteria of claim 1;
  b) growing said bacteria until said bacteria secrete fatty acids into said culture broth; and
  c) collecting said fatty acids.

14. The method of claim 13, wherein said culture broth is acidified.

15. The method of claim 13, further comprising supplementing said culture broth with 0.1-1% acetic acid.

16. The method of claim 13, wherein collecting said fatty acids comprises collecting a solid fraction of said fatty acids by filtration of said culture broth.

17. The method of claim 13, wherein collecting said fatty acids comprises extracting solids from the walls of said container with a hydrophobic solvent.

18. The method of claim 13, wherein collecting said fatty acids comprises rinsing said walls with an alkali solution.

19. The method of claim 13, wherein collecting said fatty acids comprising skimming said fatty acids from a top of said culture broth.

20. A method of making short chain fatty acids, comprising:
  a) inoculating culture broth in a container having walls with a bacteria of claim 12;
  b) growing said bacteria until said bacteria secrete fatty acids into said culture broth; and
  c) collecting said fatty acids.

* * * * *